United States Patent
Shime

(10) Patent No.: US 10,514,326 B2
(45) Date of Patent: Dec. 24, 2019

(54) POWDER SAMPLING VESSEL AND SAMPLING METHOD

(71) Applicant: Toyo Engineering Corporation, Chiyoda-ku, Tokyo (JP)

(72) Inventor: Hideki Shime, Narashino (JP)

(73) Assignee: TEC PROJECT SERVICES CORPORATION, Narashino-shi, Chiba (JP)

( * ) Notice: Subject to any disclaimer, the term of this patent is extended or adjusted under 35 U.S.C. 154(b) by 153 days.

(21) Appl. No.: 15/910,409

(22) Filed: Mar. 2, 2018

(65) Prior Publication Data

US 2018/0259427 A1   Sep. 13, 2018

(30) Foreign Application Priority Data

Mar. 10, 2017 (JP) .................. 2017-045700

(51) Int. Cl.
*G01N 1/08* (2006.01)
*G01N 1/12* (2006.01)
*G01N 1/10* (2006.01)
*G01N 33/00* (2006.01)

(52) U.S. Cl.
CPC .................. *G01N 1/08* (2013.01); *G01N 1/12* (2013.01); *G01N 2001/1037* (2013.01); *G01N 2033/0091* (2013.01)

(58) Field of Classification Search
CPC ............... G01N 1/08; G01N 2001/085; G01N 2001/1006; G01N 2033/0091
See application file for complete search history.

(56) References Cited

U.S. PATENT DOCUMENTS

| | | | |
|---|---|---|---|
| 2,688,877 A | 9/1954 | Peine | |
| 3,080,760 A | 3/1963 | Piersma | |
| 3,169,403 A * | 2/1965 | McGinn | G01N 1/08 73/864.63 |
| 5,440,941 A * | 8/1995 | Kalidindi | G01N 1/08 73/864.64 |
| 5,476,017 A * | 12/1995 | Pinto | G01N 1/08 73/864.62 |
| 6,910,393 B2 | 6/2005 | Muzzio et al. | |

FOREIGN PATENT DOCUMENTS

JP   05-288652 A   11/1993

OTHER PUBLICATIONS

European Search Report for corresponding application No. 18159044.9, dated Jul. 23, 2018 (5 pages).

* cited by examiner

*Primary Examiner* — Justin N Olamit
(74) *Attorney, Agent, or Firm* — Flynn Thiel, P.C.

(57) ABSTRACT

A sampling vessel which can prevent the operator from being exposed to a powder. A metal sampling vessel (1) for sampling powder has a cylindrical body (2) having a closed first end (2a), an opposite second end (2b) including an opening and a cavity (3), and a connector (6a, 6b) for connecting the cylindrical body (2) to a hanging line. The cylindrical body (2) satisfies a relationship M1>M2, wherein M1 represents the mass between the first end (2a) and a bottom (3c) of the cavity and M2 represents the mass between the opening (5) at the second end and the bottom (3c) of the cavity.

15 Claims, 3 Drawing Sheets

POWDER SAMPLING VESSEL AND SAMPLING METHOD

FIELD OF THE INVENTION

The present invention relates to a vessel for sampling a powder, including highly active pharmacological substances such as pharmaceutical raw materials and agrochemical raw materials, and a method for sampling a powder using the same.

BACKGROUND OF THE INVENTION

In a manufacturing site for pharmaceuticals and agrochemicals, such as a cleanroom, highly active pharmacological substances such as pharmaceutical raw materials and agrochemical raw materials are used. It is necessary to prevent the operator from being exposed to hazardous, highly active pharmacological substances due to dusting that may occur during sampling.

JP-A H5-288652 describes an invention of a powder or particulate sampler which can increase the representativeness of a sample when collecting the sample from a container 1 containing a powder or particulate material 2.

SUMMARY OF THE INVENTION

The present invention aims to provide a sampling vessel which can sample a powder under a closed environment and a sampling method using the same.

The present invention proposes a metal sampling vessel for sampling a powder, comprising:

a cylindrical body having a closed first end, an opposite second end including an opening, a cavity communicating with the opening, and a weight part extending between a bottom of the cavity and the first end; and a connector for connecting the cylindrical body to a hanging line, wherein the cylindrical body satisfies a relationship M1>M2, wherein M1 represents a mass of the weight part extending between the bottom of the cavity and the first end and M2 represents a mass of the cylindrical body extending between the opening at the second end and the bottom of the cavity. A powder sampling method using the sampling vessel and utilizing gravity is also proposed.

With the powder sampling vessel and the powder sampling method using the same according to the present invention, the operator is prevented from being exposed to the powder during sampling.

BRIEF DESCRIPTION OF THE DRAWING FIGURES

DETAILED DESCRIPTION OF THE INVENTION

<Sampling Vessel>

Figure 1:
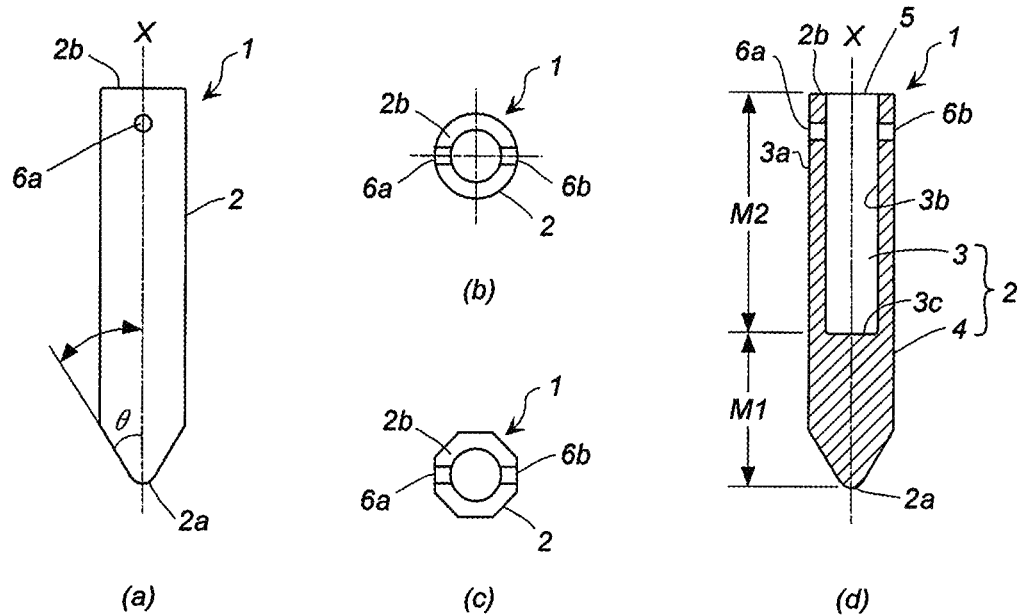
FIG. 1 shows (a) a front view of a sampling vessel of the present invention, (b) a plan view of (a) when it has a circular cross-section in a lateral direction, (c) a plan view of (a) when it has an octagonal cross-section in a lateral direction, and (d) a longitudinal cross-section of (a).

(1) Sampling Vessel of FIG. 1

A sampling vessel 1 shown in FIG. 1 is made of a metal, preferably a stainless steel such as SUS304 or SUS316.

The sampling vessel 1 shown in FIG. 1 is used for sampling a powder. The powder may have any size which can be sampled with the sampling vessel 1 shown in FIG. 1, and the size of the sampling vessel 1, such as the size of the opening or the depth of the cavity, may be adjusted to accommodate the size of the powder. Further, the powder may have a size which may not be sampled as it is with the sampling vessel 1 shown in FIG. 1, as far as it can easily collapse into a powder to enable sampling upon application of an external force.

The sampling vessel 1 has a cylindrical body 2. The cylindrical body 2 is preferably integrally molded from a single metal material. The cylindrical body 2 is closed at a first end 2a, formed with an opening 5 at an opposite second end 2b, and includes a cavity 3 communicating with the opening 5 and a weight part 4 extending between a bottom 3c of the cavity 3 and the first end 2a. The second end 2b includes an annular end face around the opening 5.

The cylindrical body 2 may have a circular, elliptical, or polygonal (such as tetragonal or hexagonal) cross section in a lateral direction that is orthogonal to the axis X. FIG. 1(b) shows a circular cross section and FIG. 1(c) shows an octagonal cross section. Hereinafter, a sampling vessel having a circular cross section as shown in FIG. 1(b) will be referred to as the sampling vessel of FIG. 1.

The cylindrical body 2 is conical at the first end 2a and its vicinity, but it may also be planar or spherical. If the first end 2a is conical, it may be pointed or rounded as shown in FIG. 1(a). If it is conical, it may have a half vertex angle $\theta$ in a range of 20° to 40°, for example about 30°.

Preferably, a periphery of the opening 5 of the cylindrical body 2, for example the edges of the annular end face, may be chamfered to round corners to facilitate cleaning.

The cavity 3 is a space for collecting powder during sampling, and may have a circular, elliptical, or polygonal (such as tetragonal or hexagonal) cross section in a lateral direction that is orthogonal to the axis X. Preferably, the cross section is circular in view of removability of powder from the cavity 3 after sampling, as well as cleanability for reuse. The internal profile of the annular end face of the second end 2b is thus preferably circular, but the outer profile may be circular, elliptical or polygonal.

The volume of the cavity 3 may be adjusted in accordance with the amount of powder to be sampled. The volume of the cavity 3 may be adjusted by the length of the cylindrical body 2, i.e., the depth of the cavity 3, the size of the opening 5, i.e., the size of the inner diameter of the cavity 3, or the like.

In the sampling vessel 1 shown in FIG. 1, the outer diameter of the cylindrical body 2, i.e., the outer diameters of the portions corresponding to the cavity 3 and the weight part 4, and the inner diameter of the cylindrical body, i.e., the inner diameter of the cavity 3, are respectively uniform in the axial direction. Preferably, the interior of the cavity 3 is chamfered to round corners to facilitate cleaning.

In the cylindrical body 2, the mass of the weight part 4 (M1) extending between the first end 2a and the bottom 3c of the cavity 3 and the mass (M2) between the opening 5 at the second end 2b and the bottom 3c of the cavity 3 satisfy the relationship M1>M2. As the portions of the cylindrical body 2 corresponding to the weight part 4 and the cavity 3 satisfy the relationship M1>M2, the sampling vessel 1 makes a vertical drop during sampling, with the first end 2a first, and plunges into the powder.

The mass ratio of M2 to M1 (M2/M1) is preferably in the range of 0.3 to 0.9, more preferably in the range of 0.6 to 0.8.

The surface of the cylindrical body 2, i.e., an outer surface 3a and an inner surface 3b of the portion corresponding to the cavity 3, and an outer surface of the weight part 4, are preferably treated by polishing for the removability of the powder from the cavity 3 after sampling and for cleanability after sampling for reuse. The annular end face of the second end 2b may also be treated by polishing.

Preferably, the polishing treatment of the surface of the cylindrical body 2 is made until a mirror surface finish or similar condition is reached. The polishing treatment may be made by way of buff polishing using a buff powder (e.g., #400 buff powder) or electrolytic polishing.

The cylindrical body 2 has a connector in the vicinity of the opening 5 for connecting the cylindrical body 2 to a hanging line. In the embodiment shown in FIG. 1, the connector to the hanging line comprises two through holes 6a and 6b extending in the thickness direction of the cylindrical body 2 between the outer surface 3a and the inner surface 3b. The through holes 6a and 6b communicate with the cavity 3. There may be one or three or more through holes to serve as the connector to the hanging line. Preferably, the through holes 6a and 6b are chamfered to round corners to facilitate cleaning.

The connector to the hanging line may be selected from, in addition to the through holes 6a and 6b shown in FIG. 1, one or a plurality of hooks attached to the second end 2b of the cylindrical body 2 for connection to the hanging line, one or a plurality of rings attached to the second end 2b of the cylindrical body 2 for connection to the hanging line, or a combination of the through holes, hooks and rings.

Further, the connector to the hanging line may be a structure in which the hanging line is tied to the cylindrical body 2 by inserting an end of the hanging line into an annular groove formed peripherally of the outer surface of the cylindrical body 2 or a structure in which the hanging line is tied to the cylindrical body 2 by latching an end of the hanging line to a flange formed at the opening 5 of the cylindrical body 2.

(2) Sampling Vessels of FIGS. 2(a) to 2(c)

Sampling vessels shown in FIGS. 2(a) to 2(c) are embodiments in each of which the annular end face around the opening 5 at the second end 2b of the cylindrical body 2 is a sloped surface.

A sampling vessel 1A of FIG. 2(a) is the same as the sampling vessel 1 shown in FIG. 1, with the exception that the annular end face of the second end 2b is sloping downwardly from the outer surface 3a to the inner surface 3b of the cylindrical body 2. As used herein, the terms "up" and "down" refer to directions when the sampling vessel is placed vertically along the axis X, with the second 2b up and the first end 2a down.

As the second end 2b of the cylindrical body 2 of the sampling vessel shown in FIG. 2(a) is an inwardly sloping annular sloped end face, when a powder is attached to the second end (annular sloped end face) 2b, it tends to fall into the interior of the sampling vessel 1 (interior of the cavity 3).

A sampling vessel 1B of FIG. 2(b) is the same as the sampling vessel 1 shown in FIG. 1, with the exception that the annular end face of the second end 2b slopes downwardly from the inner surface 3b to the outer surface 3a of the cylindrical body 2.

As the second end 2b of the cylindrical body 2 of the sampling vessel shown in FIG. 2(b) is an outwardly sloping annular sloped end face, when a powder is attached to the second end (annular sloped end face) 2b, it tends to fall outside of the sampling vessel 1.

A sampling vessel 10 of FIG. 2(c) is the same as the sampling vessel 1 shown in FIG. 1, with the exception that the annular end face around the opening 5 of the second end 2b slopes in one direction as a whole.

As the second end 2b of the cylindrical body 2 of the sampling vessel shown in FIG. 2(c) is an elliptical sloped end face which slopes in the same direction as a whole, when a powder is attached to the second end (elliptical sloped end face) 2b, it tends to fall into the interior (interior of the cavity 3) or outside of the sampling vessel 1.

(3) Sampling Vessels of FIGS. 3(a) and 3(b)

A sampling vessel 10 shown in FIG. 3(a) is the same as the sampling vessel 1 shown in FIG. 1, with the exception that the outer diameter r1 (the outer diameter of a portion having a uniform outer diameter) of a weight part 14 of a cylindrical body 12 on the side of a first end 12a and the diameter r2 of an opening 15 at a second end 12b satisfy the relationship r2>r1.

As the cylindrical body 12 has a cavity 13 and the weight part 14, and the cavity 13 communicates with the opening 15, the volume of the cavity 13 is increased when the relationship r2>r1 is sufficed. Two through holes 16a and 16b for connection to a hanging line are formed in the vicinity of the opening 15 of the cylindrical body 12 to extend in the thickness direction.

In the sampling vessel 10, a portion of the cylindrical body 12 corresponding to the cavity 13 has outer and inner diameters that continuously enlarge from a bottom 13c toward the opening 15 to define a sloped surface.

In the cylindrical body 12, the mass of the weight part 14 (M11) extending between the first end 12a and the bottom 13c of the cavity 13 and the mass (M12) between the opening 15 at the second end 12b and the bottom 13c of the cavity 13 satisfy the relationship M11>M12. The mass ratio of M12 to M11 (M12/M11) is preferably in a range of 0.3 to 0.9, more preferably in a range of 0.6 to 0.8.

A sampling vessel 20 shown in FIG. 3(b) is the same as the sampling vessel 1 shown in FIG. 1, with the exception that an outer diameter r11 at a portion having a uniform outer diameter of a weight part 24 of a cylindrical body 22 on the side of a first end 22a and a diameter r12 of an opening 25 of a second end 22b satisfy the relationship r12>r11.

As the cylindrical body 22 has a cavity 23 and the weight part 24, and the cavity 23 communicates with the opening 25, the volume of the cavity 23 is increased when the relationship r12>r11 is satisfied. Two through holes 26a and 26b for connection to a hanging line are formed in the vicinity of the opening 25 of the cylindrical body 22 to extend in the thickness direction.

In the sampling vessel 20, portions of the cylindrical body 22 corresponding to the cavity 23 includes, in a direction from the weight part 24 toward the opening 25, a small diametrical portion 23a, a sloped portion 23b, and a large diametrical portion 23c. The outer and inner diameters of the small diametrical portion 23a are larger than the outer diameter of the large diametrical portion 23c. The outer and inner diameters of the sloped portion 23b increase from the small diametrical portion 23a to the large diametrical portion 23c.

In the cylindrical body 22, the mass of the weight part 24 (M21) extending between the first end 22a and the bottom 23c of the cavity 23 and the mass (M22) between the opening 25 at the second end 22b and the bottom 23c of the cavity 23 satisfy the relationship M21>M22. The mass ratio of M22 to M21 (M12/M11) is preferably in a range of 0.3 to 0.9, more preferably in a range of 0.6 to 0.8.

Figure 2:
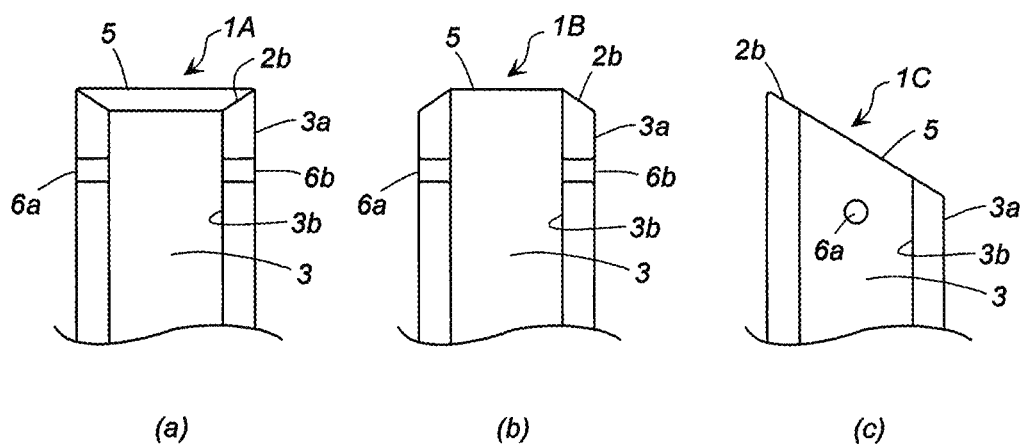
FIG. 2 shows longitudinal cross-sections (a)-(c) of sampling vessels of other embodiments whose openings have different shapes than that of the sampling vessel of FIG. 1.
Figure 3:
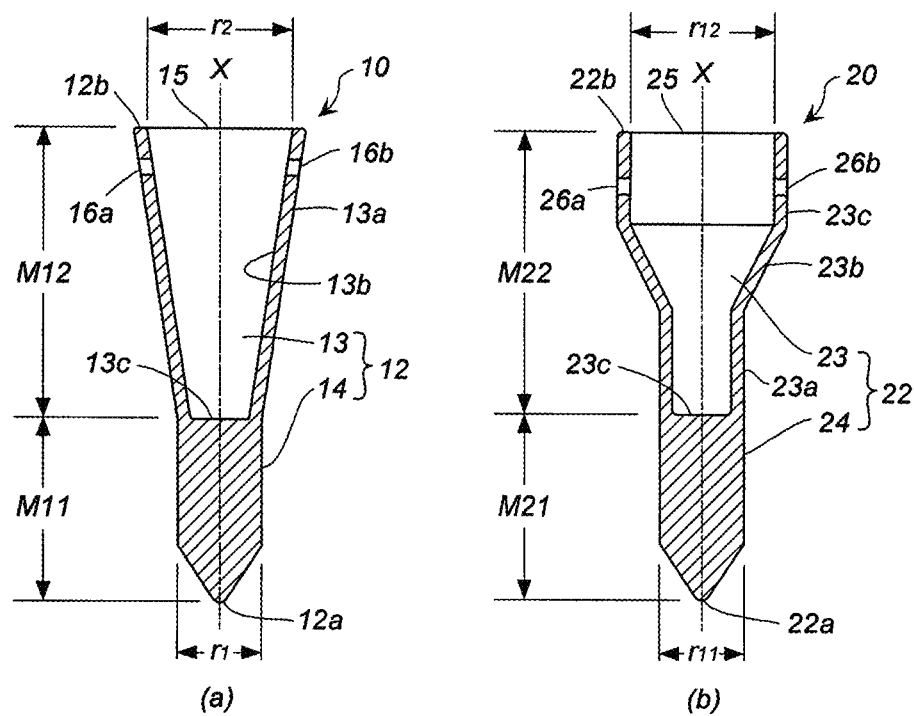
FIG. 3 shows longitudinal cross-sections (a) and (b) of sampling vessels of other embodiments whose whole shapes are different than that of the sampling vessel of FIG. 1.

The sampling vessels 1(1A-1C), 10 and 20 shown in FIGS. 1-3 are effective for sampling a powder of highly active pharmacological substances including pharmaceutical raw materials and agrochemical raw materials, as well as other chemical substances.

<Power Sampling Method>

A method for sampling a powder contained in a powder container using the sampling vessel 1 of FIG. 1 of the present invention will now be described with reference to FIG. 4. The powder sampling method of the present invention may be divided into a sampling preparation stage and a sampling implementation stage.

The sampling preparation stage may include first to fourth preparation steps.

In the first preparation step, a transparent operation container 60 which can be made airtight is prepared. The operation container 60 includes at least one opening 61, at least one pocket (not shown) formed internally, and gloves 62 into which hands may be inserted from the exterior to perform operations therein.

As the operation container 60, a flexible enclosure may be used, and a hard isolator may also be used depending on the degree of risk of the operation. In FIG. 4, a flexible enclosure is used as the operation container, and the enclosure is suspended from a ceiling 70 by two wires 65.

In the second preparation step, at least one sample bottle is placed into the pocket of the operation container 60. The sample bottle may be made of glass or plastics.

Alternatively, if the operation container 60 is made of a material which does not cause a problem upon contact with the powder raw material in terms of quality control, the pocket provided in the operation container 60 may be used in lieu of the sample bottle. The second preparation step may be conducted in parallel with the first preparation step.

In the third preparation step, after connecting to a hanging line 30, the sampling vessel 1 is inserted into the interior of the operation container 60 through the opening 61, and the gloves 62 are used to hold the hanging line 30 together with the sampling vessel 1. The hanging line 30 may be a non-braided string line such as a single strand of wire or steel line bridging between the two through holes 6a and 6b of the sampling vessel 1.

Figure 4:
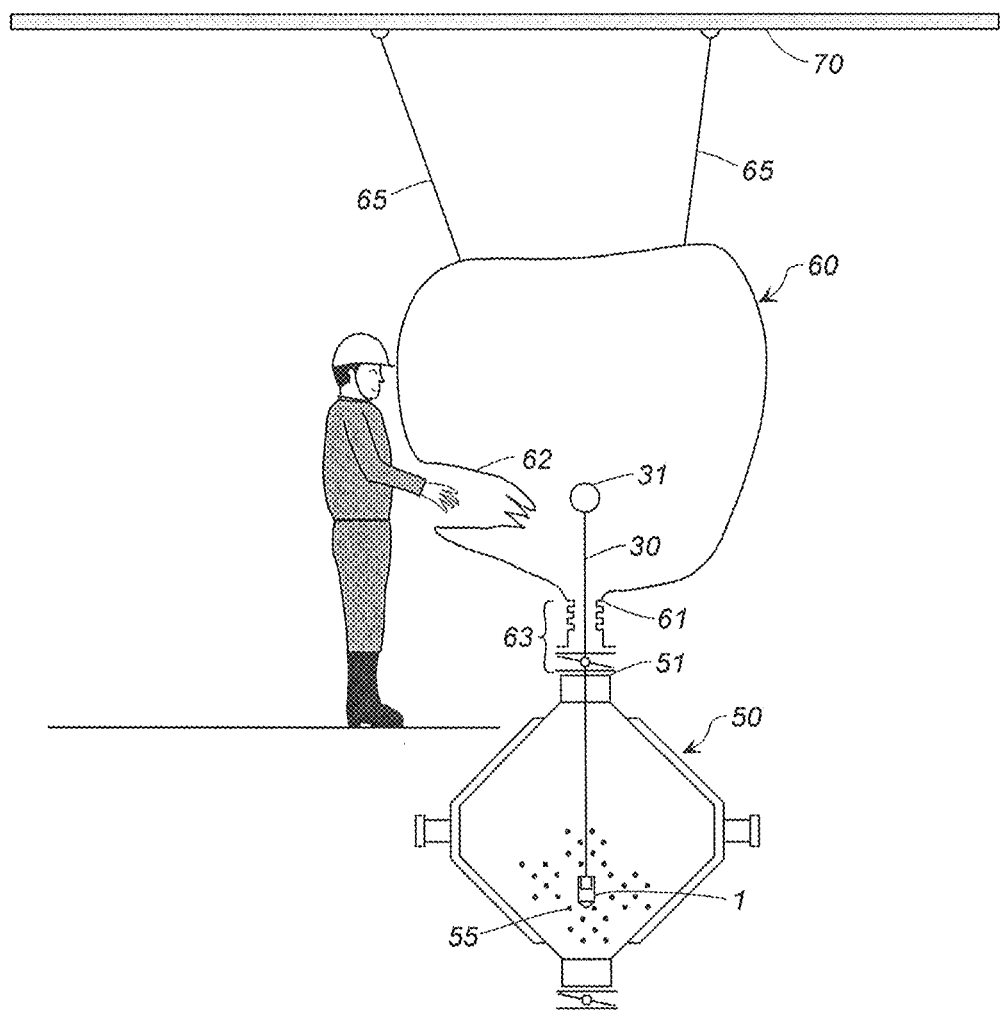
FIG. 4 shows a diagram explaining a sampling method of the present invention.

In FIG. 4, an electric reel 31 is attached to the end of the hanging line 30. The winding may be made manually, rather than by the reel, if the distance to the surface of the powder material is short.

In the fourth preparation step, the opening 61 of the operation container 60 and an opening 51 of a powder container 50 are connected together to keep the interior of the operation container 60 airtight. The powder container 50 may have a container body made of a metal or the like and an opening with a cap. In FIG. 4, a conical dryer is used and a powder (a powder of a highly active pharmacological substance) 55 is contained therein.

The connection between the opening 61 of the operation container 60 and the opening 51 of the powder container 50 is made in an air-tight manner, and a connecting adapter 63 having a structure to keep the sealed state may be used. The first to third preparation steps and the fourth preparation step may be conducted by different operators or by a single operator.

The sampling implementation stage may include first to fifth implementation steps.

In the first implementation step, with the gloves 62 holding the hanging line 30 (or the electric or manual reel 31) connected to the sampling vessel 1, only the sampling vessel 1 is dropped freely into the powder 55 contained in the powder container 50 for sampling the powder 55 in the cavity 3 of the sampling vessel 1. As the sampling vessel 1 is made of a metal (e.g., stainless steel) and thus is heavy, the mass of the portion of the cylindrical body 2 (M2) corresponding to the cavity 3 and the mass of the weight part 4 (M1) satisfy the relationship M1/M2, the first end 2a is conically shaped, and the like, the sampling vessel 1 is plunged into the powder 55 when the sampling vessel 1 is dropped freely. As a result, the powder 55 enters into the cavity 3 from the opening 5 and thus is sampled (this state is shown in FIG. 4).

When the sampling vessel 10 shown in FIG. 3(a) or the sampling vessel 20 shown in FIG. 3(b) is used in place of the sampling vessel 1, the larger diameter of the opening at the second end facilitates the sampling, as compared with the sampling vessel 1. For example, if the morphology of the powder to be sampled contained in the powder container 50 is flakes or large particles (they are however shattered upon application of external forces), the use of the sampling vessel 10 shown in FIG. 3(a) or the sampling vessel 20 shown in FIG. 3(b) facilitates the sampling and thus is preferred.

If the powder does not present a problem in terms of the shape of the sampling vessel 1, the volume of the cavity 3 may be adjusted by increasing the depth of the cavity 3 from the opening 5 to the bottom 3c or by thinning the wall thickness of the portion of the cylindrical body 2 corresponding to the cavity 3 as shown in FIG. 1(b).

In the second implementation step, the hanging line 30 held with the gloves 62 is pulled, for example by operating the electric or manual reel 31, for lifting the sampling vessel 1 from the powder container 50 into the operation container 60. In this instance, the use of the sampling vessels 1A-1C shown in FIGS. 2(a)-2(c) is preferred, as the powder 55 disposed on the second end 2b may fall within or outside the sampling vessel during the lifting of the sampling vessels 1A-1C before being carried into the operation container 60, and may remain within the powder container 50.

In the third implementation step, after holding the sampling vessel 1 lifted into the operation container 60 with the gloves 62, the sample bottle is removed from the pocket of the operation container 60, and the powder 55 of the sampling vessel 1 is transferred into the sample bottle. After transferring the powder 55 of the sampling vessel 1 into the sample bottle, the sample bottle is capped.

In the case of the sampling vessel 1A or 1C of FIG. 2(a) or 2(c), the periphery of the opening 5 includes an end face sloping from the outside to the inside, and this is preferable in terms of easiness in pouring the powder 55 into the sample bottle. In the case of the sample bottle 1B of FIG. 2(b), the wall thickness of the cylindrical body 2 is thin around the opening 5, and this is preferable in terms of easiness in inserting the opening 5 into the sample bottle.

In the fourth implementation step, the sample bottle is placed into the pocket of the operation container 60, and the sample bottle is collected, while the sampling vessel 1 is being held with the gloves 62 or placed in a pocket. When placing the sampling vessel 1 in the pocket, the pocket may be the same pocket as the sample bottle or may be a separate pocket. The sample bottle may be collected by clipping and cutting the pocket of the operation container 60.

After the series of sampling and collecting operations are complete, the connection between the operation container 60 and the powder container 50 is released. Prior to releasing the connection, the opening 61 of the operation container 60 and the opening 51 of the powder container 50 are closed to make the respective interiors airtight. The operations to close the opening 61 of the operation container 60 and the opening 51 of the powder container 50 for making the respective interiors airtight may be conducted by a different operator than the operator handling the sampling vessel 1 or by the same single operator. The third implementation step and the fourth implementation step may be conducted as one implementation step.

In the fifth implementation step, the sampling vessel 1 collected in the fourth implementation step is brought to an analysis room while keeping the sampling vessel 1 airtight. After the series of closed sampling operations are complete, the wires 65 are disconnected and the operation container 60 is removed from above the powder container 50.

By going through the aforementioned preparation stage and the implementation stage, the operator is prevented from being exposed to the powder of the highly active pharmacological substance contained in the powder container 50.

The sampling vessel 1 may be disconnected from the hanging line 30 and reused after cleaning. As the hanging line 30 may have powder attached thereto at portions close to the sampling vessel 1, it may be incinerated if made of plastics like fishlines, and may be reused after cleaning if made of a wire strand or non-braided steel string. If the electric or manual reel 31 is used, it may be reused after cleaning. The operation container 60 may be incinerated.

The powder sampling vessel and the powder sampling method using the same according to the present invention can be used for sampling highly active pharmacological substances such as pharmaceutical raw materials and agrochemical raw materials.

The invention claimed is:

1. A metal sampling vessel for sampling powder, comprising:
   a cylindrical body having a closed first end, an opposite second end including an opening, a cavity communicating with the opening, and a weight part extending between a bottom of the cavity and the first end; and
   a connector for connecting the cylindrical body to a hanging line,
   wherein the cylindrical body satisfies a relationship M1>M2, wherein M1 represents a mass of the weight part extending between the bottom of the cavity and the first end and M2 represents a mass of the cylindrical body extending between the opening at the second end and the bottom of the cavity.

2. The sampling vessel of claim 1, wherein, in the cylindrical body, a mass ratio of M2 to M1 (M2/M1) is in a range of 0.3 to 0.9.

3. The sampling vessel of claim 1, wherein the connector for connecting the cylindrical body to the hanging line is selected from one or a plurality of holes formed in the cylindrical body at the second end for connection to the hanging line, one or a plurality of hooks attached to the second end of the cylindrical body for connection to the hanging line, one or a plurality of rings attached to the second end of the cylindrical body for connection to the hanging line, or a combination of the holes, hooks and rings.

4. The sampling vessel of claim 1, wherein an outer surface and an inner surface of the cylindrical body are treated by polishing.

5. The sampling vessel of claim 1, wherein the cylindrical body has a circular or polygonal cross section in a lateral direction and the cavity has a circular cross section in the lateral direction.

6. The sampling vessel of claim 1, wherein the first end of the cylindrical body is conically shaped.

7. The sampling vessel of claim 1, wherein an outer diameter (r1) of the weight part of the cylindrical body at the first end and a diameter (r2) of the opening at the second end satisfy a relationship r2>r1.

8. The sampling vessel of claim 1, wherein a volume of the cavity in the cylindrical body is adjusted in accordance with an amount of powder to be sampled.

9. The sampling vessel of claim 1, wherein the cylindrical body is integrally molded from a single metal material.

10. The sampling vessel of claim 1, wherein an annular end face around the opening at the second end of the cylindrical body is a sloped surface.

11. The sampling vessel of claim 1, wherein the powder is selected from pharmacological substances including pharmaceutical raw materials and agrochemical raw materials.

12. A method for sampling powder contained in a powder container using the sampling vessel of claim 1, the powder sampling method comprising a sampling preparation stage and a sampling implementation stage:
   wherein the sampling preparation stage comprises:
   a first preparation step of providing a transparent operation container which can be made airtight, the operation container including at least one opening, at least one pocket formed internally, and gloves into which hands may be inserted from an exterior to perform operations inside;
   a second preparation step of placing at least one sample bottle into the pocket of the operation container;
   a third preparation step of inserting, after connecting the sampling vessel to a hanging line, the sampling vessel into the interior of the operation container through the opening, and holding the hanging line and the sampling vessel with the gloves; and
   a fourth preparation step of connecting the opening of the operation container and an opening of a powder container together to keep an interior of the operation container airtight, and
   wherein the sampling preparation stage comprises:
   a first implementation step of freely dropping only the sampling vessel into powder contained in the powder container, with the gloves holding the hanging line connected to the sampling vessel, for sampling the powder in the cavity of the sampling vessel;
   a second implementation step of pulling the hanging line held with the gloves for lifting the sampling vessel from the powder container into the operation container;
   a third implementation step of removing, after holding the sampling vessel with the gloves, the sample bottle from the pocket of the operation container, and transferring the powder of the sampling vessel into the sampling bottle;
   a fourth implementation step of placing the sample bottle into the pocket, and collecting the sample bottle while the sampling vessel is being held with the gloves or placed in the pocket; and
   a fifth implementation step of bringing the sampling vessel to an analysis room while keeping the sampling vessel airtight.

13. The powder sampling method of claim 12, wherein the operation container is a flexible enclosure or a hard isolator.

14. The powder sampling method of claim 12, wherein a manual reel or an electric reel is used for lifting the sampling vessel in the second implementation step.

15. The powder sampling method of claim 12, wherein, after sampling the powder, the sampling vessel is disconnected from the hanging line, cleaned and reused.

\* \* \* \* \*